United States Patent
Kahne et al.

(10) Patent No.: US 7,344,850 B2
(45) Date of Patent: Mar. 18, 2008

(54) IDENTIFICATION OF ACTIVE-SITE INHIBITORS OF GLYCOSYLTRANSFERASES USING A GENERALIZABLE HIGH-THROUGHPUT SCREEN

(75) Inventors: Suzanne Walker Kahne, Princeton, NJ (US); Daniel Kahne, Princeton, NJ (US)

(73) Assignee: Princeton University, Princeton, NJ (US)

( * ) Notice: Subject to any disclaimer, the term of this patent is extended or adjusted under 35 U.S.C. 154(b) by 357 days.

(21) Appl. No.: 10/748,335

(22) Filed: Dec. 30, 2003

(65) Prior Publication Data

US 2005/0142629 A1    Jun. 30, 2005

(51) Int. Cl.
*C12Q 1/48* (2006.01)
*C12N 9/10* (2006.01)
(52) U.S. Cl. .......................................... 435/15; 435/193
(58) Field of Classification Search ....................... None
See application file for complete search history.

(56) References Cited

U.S. PATENT DOCUMENTS 6,221,600 B1 * 4/2001 MacLeod et al. ............... 435/6
2002/0182661 A1 * 12/2002 Kahne et al. ................... 435/15

OTHER PUBLICATIONS

Branstrom et al. In Situ Assay for Identifying Inhibitors of Bacterial Transglycylase; FEMS Microbiology Letters, vol. 191 (2000) pp. 187-190.*
Helm et al. Rethinking Ramoplanin: The Role of Substrate Binding in Inhibition of Peptidoglycan Biosynthesis; J. Am. Chem. Soc. vol. 124 (2002) pp. 13970-13971.*
Lazar et al. Substrate Analogues to Study Cell-Wall Biosynthesis and its Inhibition; Current Opinion in Chemical Biology, vol. 6, Issue 6 (2002) pp. 786-793.*
Helm et al. Identification of Active-Site Inhibitors of Murg Using a Generlizable, High-Throughput Glycosyltransferase Screen; Journal of the American Chemical Society, vol. 125 (2003) pp. 11168-11169.*
Pedro M. Coutinho, et al., "An Evolving Hierarchical Family Classification for Glycosyltransferases", J. Mol. Biol. (2003) 328, 307-317.

Clifford D. Mol, et al., "Crystal Structures of Active Fully Assembled Substrate-and Product-Bound Complexes of UDP-N-Acetylmuramic Acid: -Alanine Ligase (MurC) from *Haemophilus influenzae*", Journal of Bacteriology, Jul. 2003, vol. 185, No. 14, p. 4152-4162.
Jay A. Bertrand, et al., "Crystal structure of UDP-N-acetylmuramoyl-L-alanine:D-glutamate ligase from *Escherichia coli*", The EMBO Journal, vol. 16, No. 12, pp. 3416-3425, 1997.
Ahmed Bouhss, et al., "Identification of the UDP-MurNAc-Pentapeptide: -Alanine Ligase for Synthesis of Branched Peptidoglycan Precursors in *Enterococcus faecalis*", Journal of Bacteriology, Sep. 2001, p. 5122-5127, vol. 183, No. 17.
Jean Van Heijenoort, "Recent advances in the formation of the bacterial peptidoglycan monomer unit", National Prod. Rep., 2001, 18, p. 503-519.

* cited by examiner

*Primary Examiner*—Jon P Weber
*Assistant Examiner*—Paul Martin
(74) *Attorney, Agent, or Firm*—Mathews, Shepherd, McKay & Bruneau, P.A.

(57) ABSTRACT

A method is described for identifying a compound that modulates the ability of a glycosyltransferase to bind a substrate comprising combining a glycosyltransferase, a labeled substrate, and a compound, in a reaction vessel, under conditions known to be suitable for the glycosyltransferase to bind the labeled substrate, measuring an amount of labeled substrate bound to the glycosyltransferase, and comparing the amount to a standardized amount to identify a relative increase or decrease in substrate bound glycosyltransferase, thereby identifying a compound that modulates the ability of the glycosyltransferase to bind the substrate. A composition comprising an effective amount of a compound of Formula I (the substituents of which are described herein), or a stereoisomer, or pharmaceutically acceptable salt thereof, that inhibits the ability of a glycosyltransferase to bind a substrate, in a pharmaceutically acceptable carrier is provided (I)

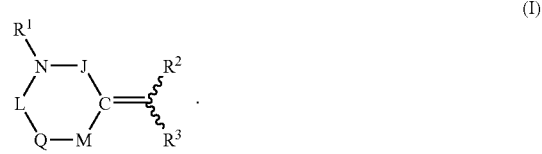

11 Claims, 9 Drawing Sheets

FIG.5 PRIOR ART

IDENTIFICATION OF ACTIVE-SITE INHIBITORS OF GLYCOSYLTRANSFERASES USING A GENERALIZABLE HIGH-THROUGHPUT SCREEN

FIELD OF THE INVENTION

The invention relates to a method for identifying a compound that modulates the biological activity of a glycosyltransferase. The invention relates to the use of a glycosyldonor displacement assay to identify compounds that inhibit glycosyltransferases. Particularly, the present invention relates to the identification of compounds as well as compounds of Formula I useful for inhibiting glycosyltransferases integral to the biosynthesis of peptidoglycan in the production of bacterial cell-walls. The present invention also relates to methods of controlling the growth of bacteria by means of applying an effective amount of a compound of Formula I.

BACKGROUND OF THE INVENTION

Peptidoglycan is a cross-linked carbohydrate polymer that forms layers around bacterial cell membranes. One of its primary functions is to protect bacterial cells from lysis due to fluctuations in internal osmotic pressure. The machinery for peptidoglycan biosynthesis is highly conserved in both Gram-negative and Gram-positive bacteria, and each of the enzymes involved in the pathway is a potential target for antibiotic chemotherapy. Walsh, C. T., Antibiotics: Actions, Origins, Resistance; ASM Press: Washington, D.C., 2003. Wong, K. K., Pompliano, D. L., Adv. Exp. Med. Biol. 1998, 456, 197-217; El Zoeiby, A., et al., Mol. Microbiol., 2003, 47, 1-12; Salmond, G. P., et al., J. Bacteriol. 1980, 144, 438-440; Ikeda, M.; Wachi, M., et al., Nucleic Acids Res. 1990, 18, 4014; Mengin-Lecreulx, D., et al., J. Bacteriol. 1991, 173, 4625-4636; Bupp, K., et al., J. Bacteriol. 1993, 175, 1841-1843; Men, H., Park, P., Ge, M., Walker, S. J. Am. Chem. Soc., 1998, 120, 2484-2485; Chen, L., Men, H., Ha, S., Ye, X.-Y., Brunner, L., Hu, Y., Walker, S. Biochemistry 2002, 41, 6824-6833; Ha, S., Walker, D., Shi, Y., Walker, S., Protein Sci. 2000, 9, 1045-1052.

MurG is a glycosyltransferase that transfers GlcNAc from UDP to the C4 hydroxyl of an N-acetyl muramic acid peptide anchored to the cytoplasmic surface of a bacterial cell membrane. Inhibitors of MurG are expected to be useful as antibiotics. However, despite considerable effort, it has generally been difficult to design good inhibitors of glycosyltransferases. Wang, R., et al., Bioorg. Med. Chem. 1997, 5, 661-672; Qian, X., et al., Carbohydr. Chem. Biol. 2000, 3, 293-312; Saotome, C., et al., Biol. 2001, 8, 1061-1070; Compain, P., et al., Med. Chem. 2001, 9, 3077-3092.; Compain, P., et al., Curr. Top. Med. Chem. 2003, 3, 541-560; Hu, Y., Chen, L., Ha, S., Gross, B., Falcone, B., Walker, D., Mokhtarzadeh, M., Walker, S. Proc. Natl. Acad. Sci. U.S.A. 2003, 100, 845-849. High-throughput screening would provide for the identification of glycosyltransferase inhibitors.

SUMMARY OF THE INVENTION

The present invention is directed to a method of identifying a compound that modulates the ability of a glycosyltransferase to bind a substrate comprising combining a glycosyltransferase, a labeled substrate, and a compound, in a reaction vessel, under conditions known to be suitable for the glycosyltransferase to bind the labeled substrate, measuring an amount of labeled substrate bound to the glycosyltransferase, and comparing the amount to a standardized amount to identify a relative increase or decrease in substrate bound glycosyltransferase, thereby identifying a compound that modulates the ability of the glycosyltransferase to bind the substrate. The invention is further directed to methods of identifying a compound that inhibits the ability of a nucleotide-sugar glycosyltransferase to bind a substrate wherein the substrate comprises UDP, TDP or GDP. The invention is further directed to methods wherein the substrate comprises UDP-GlcNac.

The invention is further directed to a composition comprising an effective amount of a compound of Formula I, or a stereoisomer, or pharmaceutically acceptable salt thereof, that inhibits the ability of a glycosyltransferase to bind a substrate, in a pharmaceutically acceptable carrier,

(I)

wherein:
J is selected from C=O, S, NH, C=S, CH$_2$, CH R$^1$, and C R$^1$R$^1$;
M is selected from C=O, S, C=S, CH R$^1$, and C R$^1$R$^1$;
L is selected from C=O, NH, C=S, S, CH R$^1$, CR$^1$R$^1$ CHR$^2$, CR$^2$R$^2$, =N—, —C(=NR$^1$)—, and —C(R$^1$)=;
Q is absent or selected from —NH—, and —NR$^1$;
R$^1$, is selected from H, C$_{1-6}$ alkyl, C$_{2-8}$ alkenyl, C$_{2-8}$ alkynyl, F, Cl, Br, I, NO$_2$, CN, (CH$_2$)$_r$OH, (CH$_2$)$_r$SH, (CH$_2$)$_r$OR$^{1d}$, (CH$_2$)$_r$SR$^{1d}$, (CH$_2$)$_r$NR$^{1a}$R$^{1a'}$, (CH$_2$)$_r$C(O)OH, (CH$_2$)$_r$C(O)R$^{1b}$, (CH$_2$)$_r$C(O)NR$^{1a}$R$^{1a'}$, (CH$_2$)$_r$NR$^{1a}$C(O)R$^{1a}$, (CH$_2$)$_r$NR$^{1a}$C(O)H, (CH$_2$)$_r$NR$^{1a}$C(O)NHR$^{1a}$, (CH$_2$)$_r$C(O)OR$^{1b}$, (CH$_2$)$_r$OC(O)R$^{1b}$, (CH$_2$)$_r$OC(O)NHR$^{1a}$, (CH$_2$)$_r$S(O)$_2$OH, (CH$_2$)$_r$S(O)$_2$NR$^{1a}$R$^{1a'}$, (CH$_2$)$_r$NR$^{1a}$S(O)$_2$R$^{1b}$, C$_{1-6}$ haloalkyl, a (CH$_2$)$_r$—C$_{3-13}$ carbocyclic residue substituted with 0-5 R$^{1c}$, and a (CH$_2$)$_r$-5-10 membered heterocyclic system containing 1-4 heteroatoms selected from N, O, and S, substituted with 0-3 R$^{1c}$;
R$^{1a}$ and R$^{1a'}$, at each occurrence, are selected from H, C$_{1-6}$ alkyl, C$_{2-8}$ alkenyl, C$_{2-8}$ alkynyl, a (CH$_2$)$_r$—C$_{3-10}$ carbocyclic residue substituted with 0-5 R$^{1e}$, and a (CH$_2$)$_r$-5-10 membered heterocyclic system containing 1-4 heteroatoms selected from N, O, and S, substituted with 0-3 R$^{1e}$;
R$^{1b}$, at each occurrence, is selected from C$_{1-6}$ alkyl, C$_{2-8}$ alkenyl, C$_{2-8}$ alkynyl, a (CH$_2$)$_r$—C$_{3-6}$ carbocyclic residue substituted with 0-2 R$^{1e}$, and a (CH$_2$)$_r$-5-6 membered heterocyclic system containing 1-4 heteroatoms selected from N, O, and S, substituted with 0-3 R$^{1e}$;
R$^{1c}$, at each occurrence, is selected from C$_{1-6}$ alkyl, C$_{2-8}$ alkenyl, C$_{2-8}$ alkynyl, (CH$_2$)$_r$C$_{3-6}$ cycloalkyl, Cl, Br, I, F, (CF$_2$)$_r$CF$_3$, NO$_2$, CN, (CH$_2$)$_r$NR$^{1f}$R$^{1f}$, (CH$_2$)$_r$OH, (CH$_2$)$_r$OC$_{1-4}$ alkyl, (CH$_2$)$_r$SC$_{1-4}$ alkyl, (CH$_2$)$_r$C(O)OH, (CH$_2$)$_r$C(O)R$^{1b}$, (CH$_2$)$_r$C(O)NR$^{1f}$R$^{1f}$; (CH$_2$)$_r$NR$^{1f}$C(O)R$^{1a}$, (CH$_2$)$_r$C(O)OC$_{1-4}$ alkyl, (CH$_2$)$_r$OC(O)R$^{1b}$, (CH$_2$)$_r$C(=NR$^{1f}$)NR$^{1f}$R$^{1f}$, (CH$_2$)$_r$S(O)$_p$R$^{1b}$, (CH$_2$)$_r$ NHC(=NR$^{1f}$)NR$^{1f}$R$^{1f}$, (CH$_2$)$_r$S(O)$_2$NR$^{1f}$R$^{1f}$, (CH$_2$)$_r$ NR$^{1f}$S(O)$_2$R$^{1b}$, and (CH$_2$)$_r$phenyl substituted with 0-3 R$^{1e}$;

$R^{1d}$, at each occurrence, is selected from $C_{1-6}$ alkyl, $C_{2-6}$ alkenyl, $C_{2-6}$ alkynyl, a $C_{3-10}$ carbocyclic residue substituted with 0-3 $R^{1c}$, and a 5-6 membered heterocyclic system containing 1-4 heteroatoms selected from the group consisting of N, O, and S substituted with 0-3 $R^{1c}$;

$R^{1e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{1f}R^{1f}$, and $(CH_2)_r$phenyl;

$R^{1f}$, at each occurrence, is selected from H, $C_{1-6}$ alkyl, and $C_{3-6}$ cycloalkyl;

R2 is selected from $(CH_2)_r$—$C_{5-10}$ carbocyclic residue substituted with 0-7 $R^{2a}$, and a $(CH_2)_r$-5-10 membered heterocyclic system optionally containing C=O and 1-4 heteroatoms selected from N, O, and S, wherein the heterocyclic system is substituted with 0-7 $R^{2a}$;

$R^{2a}$, at each occurrence, is selected from H, $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{9b}$, $(CH_2)_rC(O)NR^{1f}R^{1f}$ and $(CH_2)_r$phenyl wherein the phenyl on the $(CH_2)_r$ phenyl is substituted with 0-5 substituents selected from F, Cl, Br, I, $NO_2$, $C_{1-6}$ alkyl, OH, $(CH_2)_rC(O)OH$, $(CH_2)_rC(O)OC_{1-4}$ alkyl, $NR^{2b}R^{2b}$, and $(CH_2)_rS(O)_2 NR^{2b}R^{2b}$.

$R^{2b}$, at each occurrence, is selected from H, $C_{1-6}$ alkyl, and $C_{3-6}$ cycloalkyl; and R3 is selected from H;

alternatively $R^2$ and $R^3$ join to form a 5-10 membered heterocyclic system optionally containing C=O and 1-4 heteroatoms selected from N, O, and S, wherein the heterocyclic system is substituted with 0-7 $R^{2a}$.

DETAILED DESCRIPTION OF THE INVENTION

Unless defined otherwise, all technical and scientific terms used herein have the same meaning as is commonly understood by one of skill in the art to which this invention belongs. All publications referred to herein are incorporated by reference.

MurG is a nucleotide diphospho-glycosyltransferase (NDP-Gtf) involved in murein biosynthesis. It catalyzes the transfer of N-acetyl glucosamine (GlcNAc) from UDP-GlcNAc to Lipid I, an N-acetyl muramic acid (MurNAc) derivative that is anchored to the cytoplasmic surface of the bacterial cell membrane. The GlcNAc-MurNAc product of the MurG reaction is the minimal subunit of the peptidoglycan polymer that surrounds and protects bacterial cell membranes. MurG is an antibiotic target. Inhibitors of this target represent a novel class of antibiotics with which to combat resistant bacterial strains.

Figure 1:
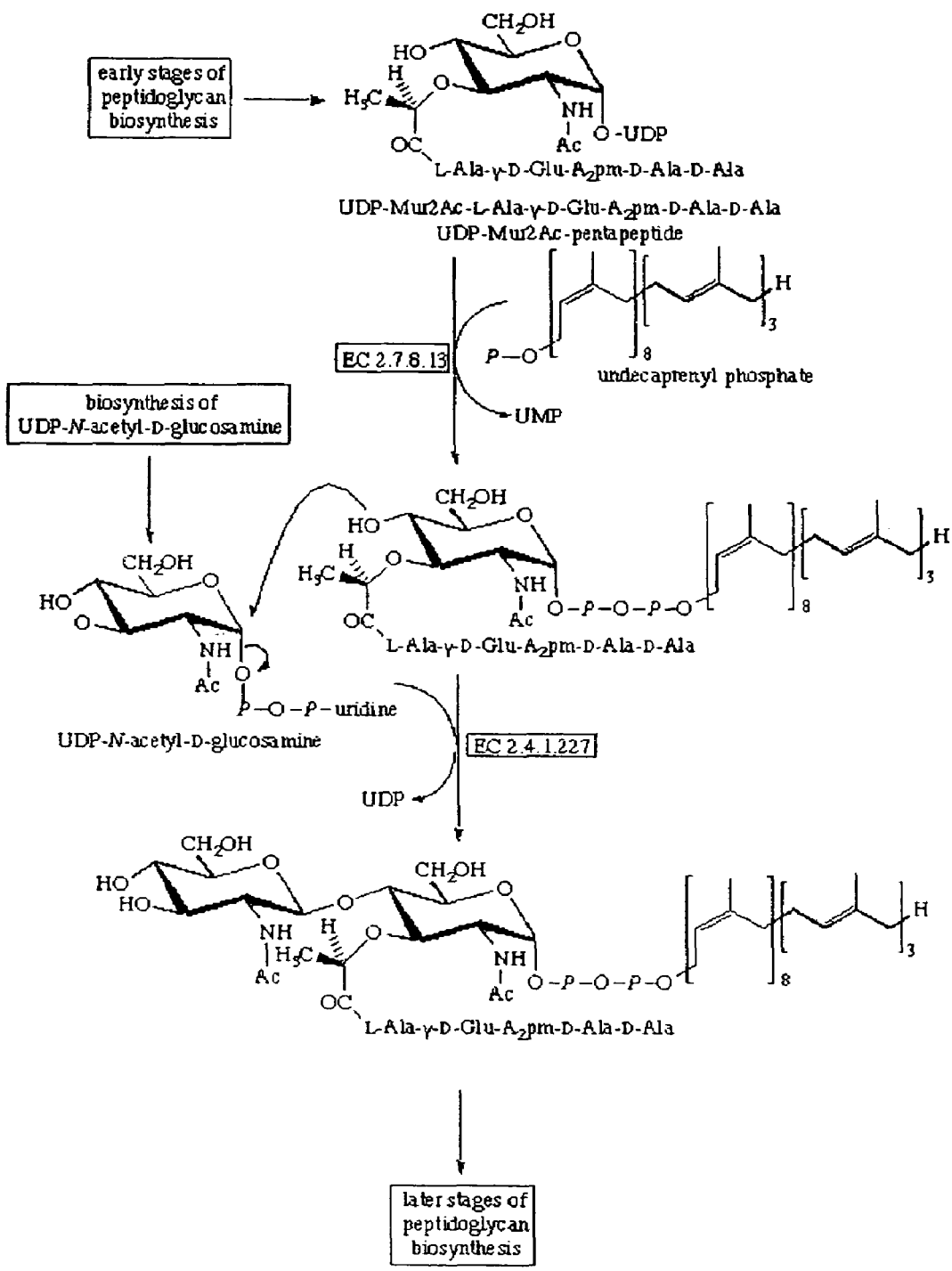
FIG. 1 displays an illustration of peptidoglycan biosynthesis wherein MurG (EC2.4. 1.227) catalyzes the reaction UDP-N-acetylglucosamine (UDP-GlcNac)+Mur2Ac(oyl-L-Ala-γ-D-GlU-L-Lys-D-Ala-D-Ala)-diphosphoundecaprenol=UDP+GlcNAc-(1→4)-Mur2Ac(oyl-L-Ala-γ-D-Glu-L-Lys-D-Ala-D-Ala)-diphosphoundecaprenol.

The term "glycosyltransferase", as used herein, refers to the superfamily of nucleotide-sugar glycosyltransferases (NDP-Gtases) that are within NC-IUBMB glycosyltransferases EC2.4.1. "Glycosyltransferase", accordingly, as used herein, for example, refers to the "Mur_" enzymes. See, e.g., *Remarkable structural similarities between diverse glycosyltransferases*, Hu, Y., Walker, S., Chem. Biol. 2002, 9, 1287-1296; *Recent advances in the formation of the bacterial peptidoglycan monomer unit*, van Heijenoort, J., Nat. Prod. Rep. 18 (2001) 503-519; VanNieuwenhze M S, et al., J Am Chem Soc. 2001 Jul. 25;123(29):6983-8; *Crystal structure of UDP-N-acetylmuramoyl-L-alanine:D-glutamate ligase from Escherichia coli*, EMBO J. 1997 Jun; 16(12):3416-25; *Peptidoglycan biosynthesis: Unexploited antibacterial targets within a familiar pathway*, Adv Exp Med Biol. 1998;456:197-217; *Crystal structures of active fully assembled substrate-and product-bound complexes of UDP-N-acetylmuramic acid:L-alanine ligase (MurC) from Haemophilus influenzae*, J Bacteriol. 2003 Jul;185(14): 4152-62; *Identification of the UDP-MurNAc-pentapeptide: L-alanine ligase for synthesis of branched peptidoglycan precursors in Enterococcus faecalis*, J Bacteriol. 2001; Sep; 183(17): 5122-7. MurG transferase (undecaprenyldiphospho-muramoylpentapeptide β-N-acetylglucosaminyltransferase (Systematic name: UDP-N-acetyl-D-glucosamine:N-acetyl-α-D-muramyl(oyl-L-Ala-y-D-Glu-L-Lys-D-Ala-D-Ala)-diphosphoundecaprenol β-1,4-N-acetylglucosaminlytransferase)) is an example of glycosyltransferase in the subject matter of the present invention. MurG (NC-IUBMB glycosyltransferase EC2.4.1.227) catalyzes the reaction UDP-N-acetylglucosamine (UDP-GlcNac)+Mur2Ac(oyl-L-Ala-γD-Glu-L-Lys-D-Ala-D-Ala)-diphosphoundecaprenol=UDP+GlcNAc-(1→4)-Mur2Ac(oyl-L-Ala-γ-D-Glu-L-Lys-D-Ala-D-Ala)-diphosphoundecaprenol. See FIG. 1.

The assay described herein is based on displacement of a fluorescently labeled glycosyl donor. The assay is based on displacement of a ligand from the glycosyl donor binding site. The donor displacement assay described herein can be adapted to screen any NDP-glycosyltransferase in which at least one substituent on the glycosyl group of the glycosyl donor can be modified to incorporate a label without abolishing binding of the donor to the glycosyltransferase. NDP-glycosyltransferases of the GT-A and GT-B superfamilies are suitable candidates for screening. For example, GnT1 (PDB#1FOA) is a UDP-GlcNAc transferase containing an exposed N-acetyl group and it can be screened for compounds that displace a labeled UDP-GlcNAc where the label is on the C2 position. The reader is particularly referred to Coutinho, P. M., et al., *An Evolving Hierarchical Family Classification for Glycosyltransferases*J. Mol. Biol., 328: 307 (2003); Liu, J., et al., Protein Science, 12(7): 1418 (2003). The results of the present invention indicate that it is possible to identify inhibitors from a donor displacement assay that are selective for one enzyme over others that use similar or identical substrates.

GTases have been identified in various genomes, and the majority of them utilize NDP-sugar donors. A large percentage of these NDP-GTases utilize UDP or TDP donors. Thus, many GTases utilize donor substrates that are similar or identical to that used by MurG. To assess the selectivity of the best MurG inhibitors, we tested them against three other enzymes that use UDP-hexose substrates. Two of these enzymes are GTases that are known (GtfB) or proposed (OGT) to be structurally related to MurG.

*E. coli* MurG is an ideal model system to address the utility of a donor displacement assay for discovering Gtf inhibitors. Using the crystal structure of the enzyme with UDP-GlcNAc bound, it was predicted which positions on the glycosyl donor can be modified without disrupting binding to the enzyme. Most of the glycosyl donor is buried in the active site cleft with numerous contacts to the enzyme. However, the methyl group of the N-acetyl moiety at C2 protrudes from the active site and makes no contacts to the enzyme. A glycosyl donor containing a fluorescent label for use in a displacement assay (F1) was designed. The ability of the fluorescent glycosyl donor to bind to MurG was evaluated by monitoring the polarization of a solution of F1(FIG. 2) during a titration with the enzyme. See, FIG. 2, FIG. 9, and Example X.

Figure 6:
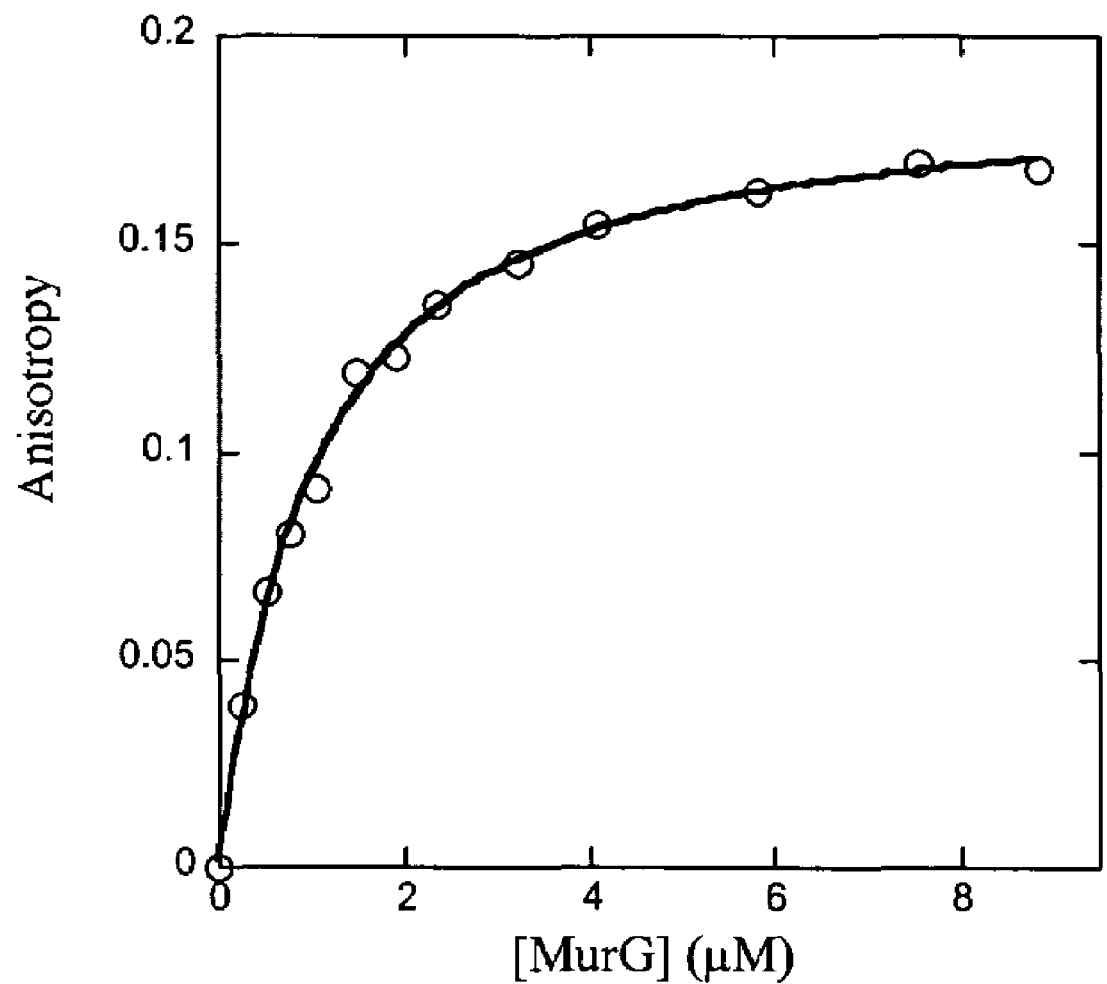
FIG. 6 displays a fluorescence anisotropy curve for 0.33 μM F1 in 50 mM HEPES, pH 8.0 as a function of MurG concentration.
Figure 7:
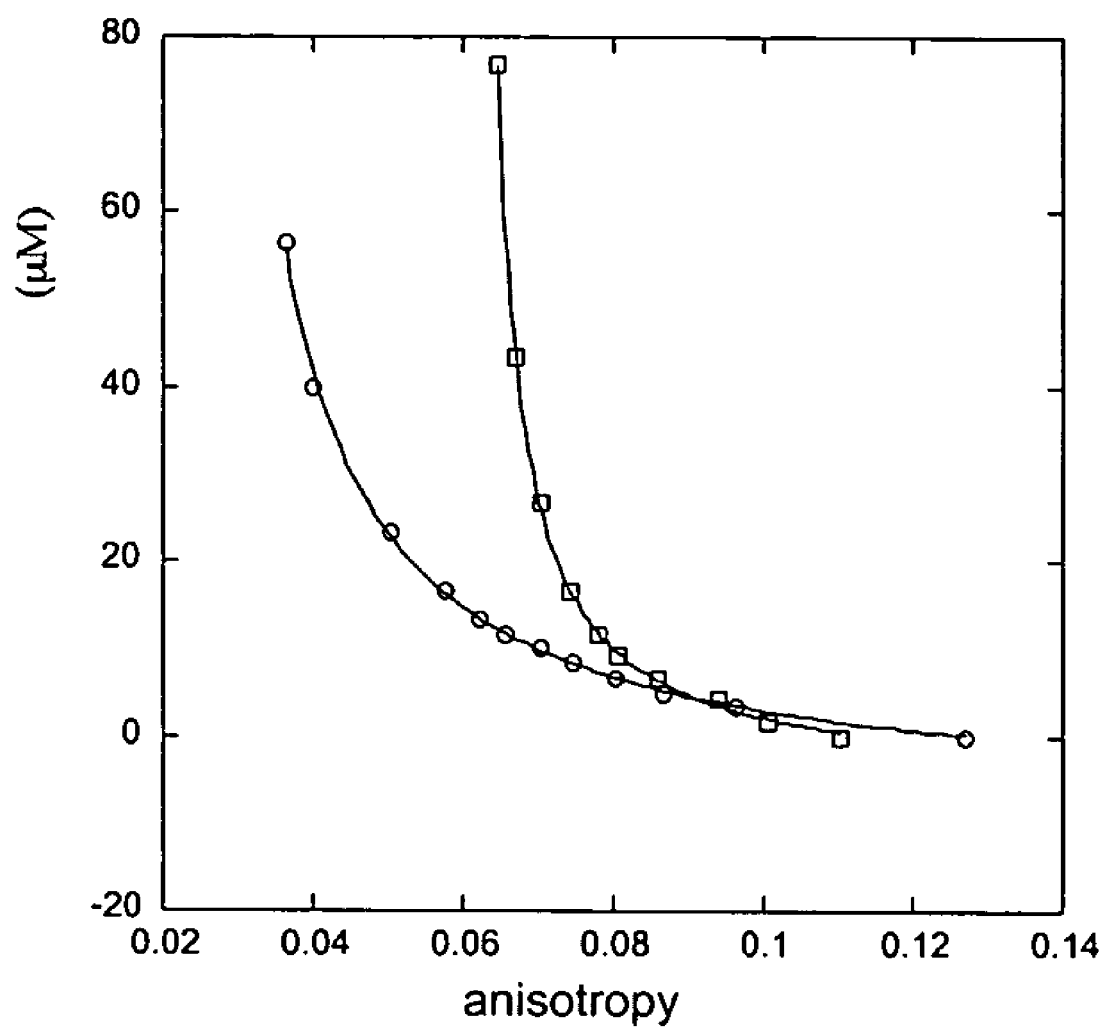
FIG. 7 displays fluorescence anisotropy of 0.33 μM F1 and 2.6 μM MurG in 50 mM HEPES (pH 8.0) as a function of competitor ligand ([UDP-GlcNAc]=□, [UDP]=o).

As shown in FIGS. 6 and 7, the polarization increases as MurG is added, indicating that F1 binds. The data fit well to an equation for 1:1 binding. A dissociation constant of 1.4±0.2 µM for the interaction was determined. Addition of UDP-GlcNAc to the MurG:F1 solution causes the polarization to drop, consistent with competitive displacement of the fluorescent donor from the active site. The binding constants of a series of compounds that are known to inhibit MurG were determined from the concentrations required to displace the fluorescent glycosyl donor, and the relative results correlate well with the $IC_{50}$'s determined previously in a kinetic assay (Table 1).

The term "substrate", as used herein, refers to a natural or synthetic substrate including analogs of substrates of a nucleotide-sugar glycosyltransferase. In the case of the MurG nucleotide-sugar glycosyltransferase example of the present invention, donor (UDP-GlcNac) (substrate) analogues containing N-acyl modifications, for example, bind to MurG. Particularly, the fluoresceinated UDP-GlcNAc (hexose donor) analogue (F1) is an example labeled substrate for use in substrate displacement assays of the present invention. See FIG. 2. Because methods of the present invention generally identify compounds that compete with diphosphate groups for binding to the active site of the nucleotide-sugar glycosyltransferase, i.e., compounds that contain structural elements that mimic the functions of the diphosphate, substrates of the nucleotide-sugar glycosyltransferases employed in methods of the present invention structurally comprise uridine diphosphate(UDP), thymidine diphosphate (TDP) or guanidine diphosphate (GDP). With reference to MurG, for example, substrate refers to, but is not limited to UDP-GlcNac. See, Jeremiah S. Helm, Yanan Hu, Lan Chen, Ben Gross, and Suzanne Walker, *Identification of Active-Site Inhibitors of MurG Using a Generalizable High-Throughput Glycosyltransferase Screen*, J. Am. Chem. Soc. 2003, 125, 11168-11169.

The term "labeled substrate", as used herein, refers to a substrate as defined herein with a detectable label associated therewith or attached thereto. An X-ray elucidated structure of a cocomplex of MurG containing UDP-GlcNAc, for example, shows that the C2 N-acetyl group on the donor is solvent exposed and the protein makes no contacts to the methyl group. Hu, Y., Chen, L., Ha, S., Gross, B., Falcone, B., Walker, D., Mokhtarzadeh, M., Walker, S., Proc. Natl. Acad. Sci. U.S.A. 2003, 100, 845-849. Accordingly, a preferred site of attachment of a label to UDP-GlcNac, for example, is at the N-acyl. The label may be any suitable labeling substance, including but not limited to a radioisotope, an enzyme, an enzyme cofactor, an enzyme substrate, a dye, a hapten, a chemiluminescent molecule, a fluorescent molecule, a phosphorescent molecule, an electrochemiluminescent molecule or a chromophore. In one embodiment, the label may be an acridinium ester (AE), e.g., 4-(2-succinimidyloxycarbonyl ethyl)-phenyl-10-methylacridinium-9-carboxyl-ate fluorosulfonate. Groups of interacting labels include, but are not limited to, enzyme/substrate, enzyme/

TABLE 1

Dissociation constants of donor sugar UDP-GlcNAc and its analogues

| Compounds | UDP-GlcNAc | F1 | UDP-GalNAc | UDP | UMP | ADP |
|---|---|---|---|---|---|---|
| Dissociation constants (µM)[a] | 1.8 ± 0.2 | 1.4 ± 0.2 | 73.1 ± 14.1 | 2.6 ± 0.2 | 99.6 ± 12.2 | 88.2 ± 26.9 |
| $IC_{50}$ (µM)[b] | — | — | >1000 | 65 ± 1 | 600 ± 50 | 1260 ± 300 |
| Signal change at 25 µM | — | 60% | 10% | 50% | <10% | <10% |

[a]Dissociation constants were measured by fluorescence polarization displacement assay.
[b]IC50 data was measured by using different assay (biotin-capture assay), in which $C_{10}$-Lipid I was used as acceptor[Ha, 1999 #29].

These initial experiments validated the displacement assay and the ability to discriminate between strong and weak binders in a high throughput assay by monitoring changes in polarization at a single concentration of compound.

cofactor, luminescent/quencher, luminescent/adduct, dye dimers and Forrester energy transfer pairs.

Figure 2:
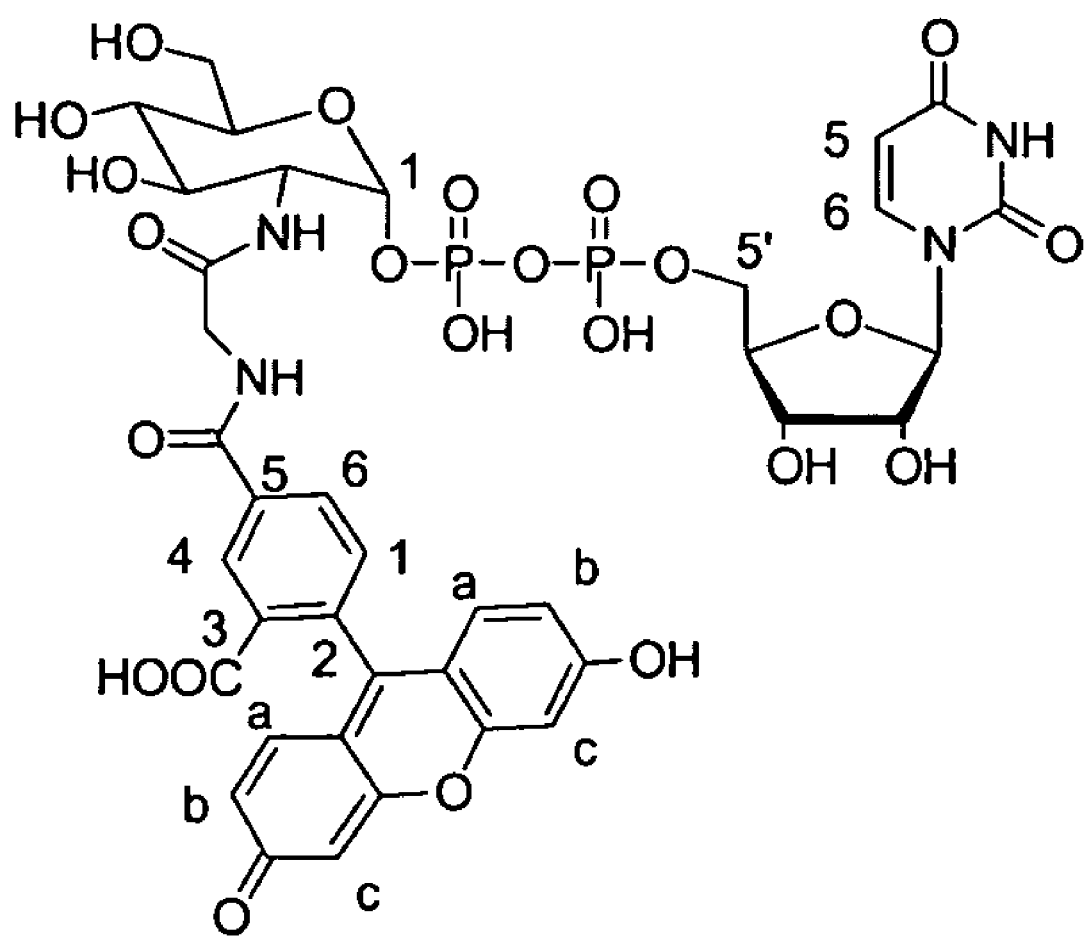
FIG. 2 shows the fluoresceinated UDP-GlcNAc (hexose donor) analogue (F1), an example labeled substrate for use in substrate displacement assays of the present invention.

With reference to MurG, for example, labeled substrate refers to, but is not limited to the fluoresceinated UDP-GlcNAc (hexose donor) analogue (F1). FIG. 2 shows this preferred example labeled substrate for use in substrate displacement assays of the present invention. The Kd of UDP-GlcNAc, for example, is identical to that of F1, accordingly, the fluorophore does not inhibit the binding of the substrate to MurG.

Methods of the present invention particularly provide the ability to distinguish weaker binders from better binders on the basis of changes in anisotropy at fixed concentrations of the labeled substrate, nucleotide-sugar glycosyltransferase, and a candidate compound based on the qualitative and/or quantitative measurement of displacement of the labeled substrate from the nucleotide-sugar glycosyltransferase active site. An example method of the present invention provides the ability to distinguish weaker binders from better binders on the basis of changes in anisotropy at fixed concentrations of F1 (FIG. 2), MurG, and a candidate compound based on the qualitative and/or quantitative measurement of displacement of the labeled substrate from the MurG active site.

The invention described herein provides methods of identifying compounds that modulate the ability of a glycosyltransferase to bind a substrate comprising combining a glycosyltransferase, a labeled substrate, and a compound, in a reaction vessel, under conditions known to be suitable for the glycosyltransferase to bind the labeled substrate, measuring an amount of labeled substrate bound to the glycosyltransferase, and comparing the amount to a standardized amount to identify a relative increase or decrease in substrate bound glycosyltransferase thereby identifying a compound that modulates the ability of the glycosyltransferase to bind the substrate. The term "standardized amount", as used herein, generally refers to a known standardized amount of labeled substrate bound to the glycosyltransferase under control conditions measured in at least one experiment. Control conditions, for example, may include merely the glycosyltransferase of interest and labeled substrate under conditions known to be suitable for the glycosyltransferase to bind the labeled substrate. Preferred control conditions additionally include, for example, the glycosyltransferase of interest (e.g., MurG), a known modulator (e.g., competitor) (e.g., UDP) of the ability of a glycosyltransferase to bind a substrate, and labeled substrate (e.g., F1), under conditions known to be suitable for the glycosyltransferase to bind the labeled substrate.

Methods described herein are used here for high-throughput screening and are simple to implement and can be readily adapted to screen any glycosyltransferase, for example, in which at least one modifiable group on the nucleotide-sugar is solvent exposed. Crystal structures of existing glycosyltransferases provide for the design of suitable fluorescent substrate analogues. Structural similarities between glycosyltransferases demonstrate that fluorescent analogues that work for one nucleotide-sugar glycosyltransferase will also work for related nucleotide-sugar glycosyltransferases. Hu, Y.; Walker, S., Chem. Biol. 2002, 9, 1287-1296. Methods described herein may also be employed to identify families of scaffolds that mimic diphosphates in different conformations. The identification of scaffolds is invaluable for the diversity-oriented synthesis of compounds for glycosyltransferase inhibition.

"Conditions known to be suitable for the glycosyltransferase to bind the labeled substrate", as used herein, refers to a system wherein the environment, including temperature and time, of the reaction is effective to sufficiently provide for the detectable binding of glycosyltransferase to substrate. Preferred conditions substantially emulate the kinetics of the reaction under physiological conditions.

The term "modulate", as used herein, e.g., in reference to the ability of a compound to modulate the ability of a glycosyltransferase to bind a substrate, refers to the ability of the compound to increase (enhance) or decrease (inhibit) the ability of a glycosyltransferase to bind a substrate. Accordingly, methods described herein are employed to identify compounds that agonize or antagonize the biological activity of a glycosyltransferase.

Methods of the present invention include Solid Phase method of identifying a compound that modulates the ability of a glycosyltransferase to bind a substrate comprising providing a glycosyltransferase attached to a solid phase, a labeled substrate, and a compound, under conditions known to be suitable for the glycosyltransferase to bind the labeled substrate, washing the solid phase, and measuring an amount of labeled substrate bound to the glycosyltransferase attached to the solid phase, and optionally comparing the amount to a standardized amount to identify a relative increase or decrease in substrate bound glycosyltransferase, thereby identifying a compound that modulates the ability of the glycosyltransferase to bind the substrate. Solid phase materials and methods suitable for use in methods of the present invention are well-known to those skilled in the art. Meldal M., Biopolymers. 2002;66(2):93-100; Dolle R E., Mol Divers. 1997;2(4):223-36.

The term "compound", as used herein, refers to test compounds and otherwise candidate modulators of the ability of a glycosyltransferase to bind a substrate, including but not limited to small molecule compounds and chemical entities. Example compounds that inhibit the activity, i.e., substrate binding of nucleotide-sugar glycosyltransferases, identified by methods described herein have strikingly similar structures. A family of MurG inhibitors, for example, is identified herein having a neutral core that mimics the diphosphate moiety of UDP-GlcNAc with respect to the display of substituent groups. Manual docking of the inhibitors into the UDP-GlcNAc binding pocket of MurG, for example, reveals that the compounds are best accommodated when the five-membered ring is located in the vicinity of the diphosphate binding site with the N-1 substituent oriented toward the GlcNAc binding site and the arylidene substituent oriented toward the uridine binding site.

Figure 8:
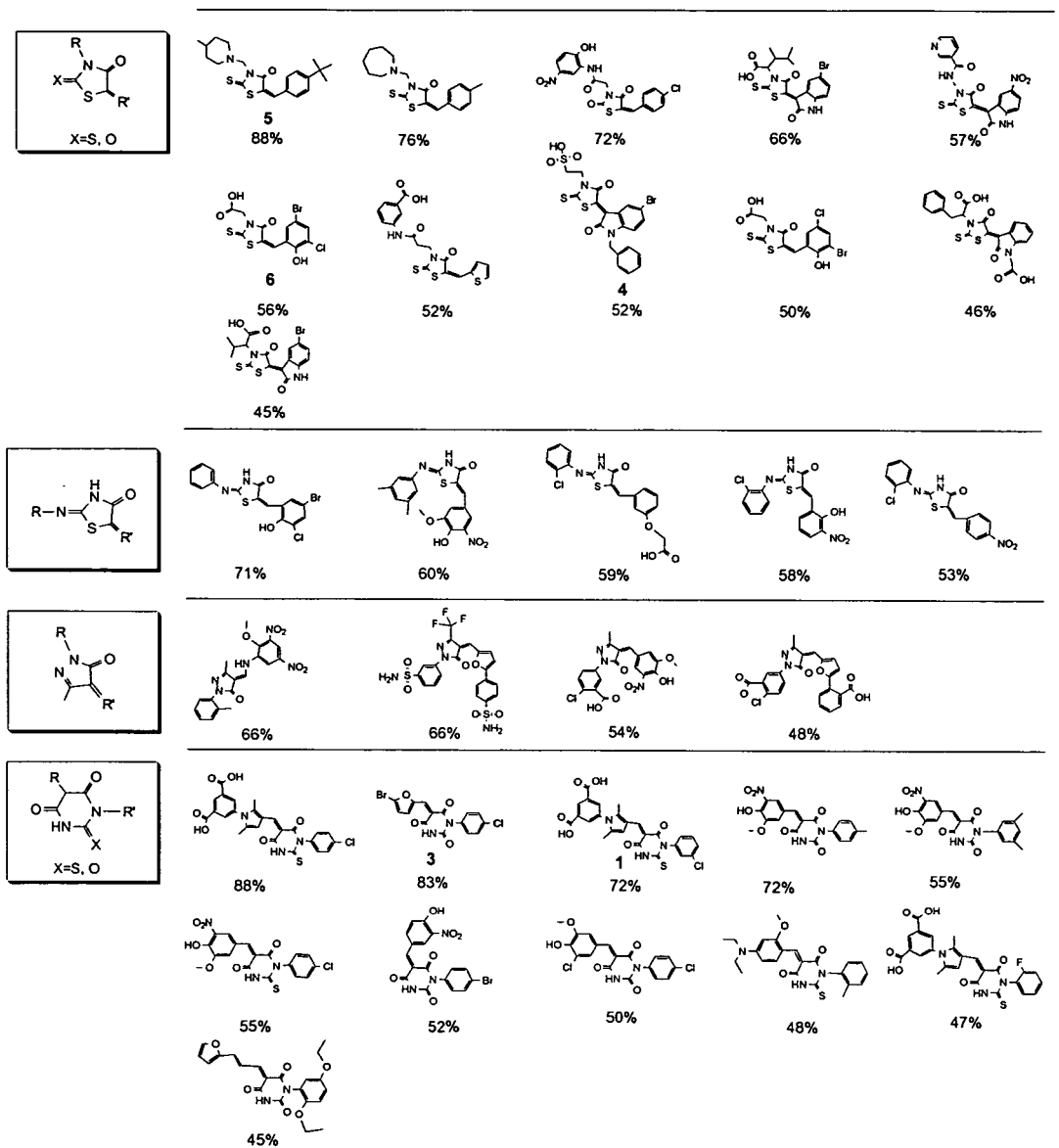
FIG. 8 shows example structures of selected compounds that caused >40% MurG inhibition at a concentration of 2.5 μg/mL (~5 μM). Conserved core structures are indicated.

Conditions (protein and fluorescent ligand concentrations) were established experimentally at which 25 µM UDP caused a 50% drop in fluorescence polarization. UDP was used to standardize conditions because it binds to MurG with a dissociation constant of 2.6±0.2 µM. Compounds are desired with comparable or better affinity. The conditions were adapted to a 20 µL scale and screening was carried out in 384-well microplates. Approximately 64,000 molecules were screened in duplicate at a concentration of 25 µg/mL of each inhibitor (molecular weights of the compounds in the library typically fell into the range of 400-600 g/mol). The molecules screened exemplified a wide range of structural diversity. Compounds that reproducibly caused a 50% or greater drop in polarization were scored as hits. 456 hits (0.6% hit rate) were identified. 220 compounds from 456 hits were selected to evaluate for MurG inhibition in a kinetic assay designed to monitor the incorporation of radioactivity into Lipid II. UDP was again used to standardize the secondary assay. Reaction conditions were chosen wherein a 5 µM concentration of UDP caused a 50% drop in product formation. Under these reaction conditions, both the UDP-GlcNAc and Lipid I concentrations are within two-fold of their $K_m$ values. Compounds, for example, having comparable or better potency than UDP, were evaluated in duplicate at a concentration of 5 µg/mL. Those that inhibited MurG by at least 40% were scored as positive. 55 out of 220 compounds (25%) met or exceeded this cutoff. The $IC_{50}$ values for these compounds were measured using the same radiometric assay. Generally, the $IC_{50}$ values of the compounds fell between 1 and 10 μM. An analysis of the screening results revealed that many of the compounds identified in the secondary screen contain a 1,3-disubstituted heterocyclic core. In fact, 31 out of the 55 compounds (56%) were found to contain one of the cores shown in FIG. 8. Reaction solution contains 14 μM UDP-$^{14}$C-GlcNAc, 15 μM $C_{20}$ Lipid I analogue 50 mM HEPES (pH=7.9), and 5 mM $MgCl_2$. Reactions were started by adding 0.5 μL of 0.01 mg/mL MurG stock (in 20 mM Tris, pH=7.9, 150 mM NaCl, and 50 mM EDTA) to the substrate solution, and were quenched after 2 min by adding 10 μL 0.1% SDS. A subset of these compounds (compounds 1, 5 and 7) were selected for further kinetic analysis and found that they were competitive inhibitors with respect to UDP-GlcNAc. Accordingly, a sugar donor-based displacement assay will yield inhibitors that bind to the same region of the enzyme as UDP-GlcNAc. Selecting compounds that bind to a single region of the enzyme simplifies the analysis of structure-activity relationships.

Selectivity

MurG is an inverting glycosyltransferase that catalyzes the formation of a beta glycosidic linkage from an alpha-linked UDP-glycosyl donor. Several other inverting glycosyltransferases that also use UDP donors were chosen to test the hits. Gtfs, O-linked GlcNAc transferase (OGT), is a eukaryotic glycosyltransferase that uses UDP-GlcNAc as a glycosyl donor. Sequence-based computational studies have suggested that OGT belongs to the same structural superfamily as MurG. The other Gtf, GtfB, is a prokaryotic Gtf involved in the biosynthesis of glycopeptide antibiotics. Its natural donor is UDP-glucose, and an X-ray structure shows that its structure is remarkably similar to that of MurG. MurA, an enolpyruvoyl transferase that converts UDP-GlcNAc to the corresponding C3 enolpyruvate derivative, and PBP1b, a prokaryotic enzyme that forms the glycan chains of peptidoglycan, were also evaluated. The substrate for PBP1b is the undecaprenyl-diphosphoryl-disaccharide donor, Lipid II. Thus, MurA uses UDP-GlcNAc, but is not a Gtf, whereas PBP1b is a Gtf that uses a diphospholipid rather than a diphosphonucleoside as a leaving group.

Each of the compounds shown in Table 2 was screened for its ability to inhibit the panel of enzymes.

TABLE 2

$IC_{50}$ of inhibitors against selected enzymes

| Compounds | $IC_{50}$ (μM) | | | | |
|---|---|---|---|---|---|
| | MurG | OGT | MurA | PBP1b | GtfB |
| 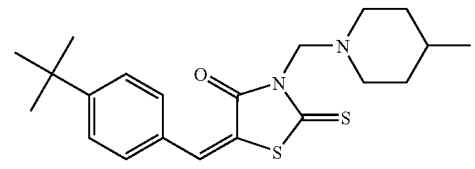 1 | 1.4 | >100* | >100* | >100* | 15 |
| 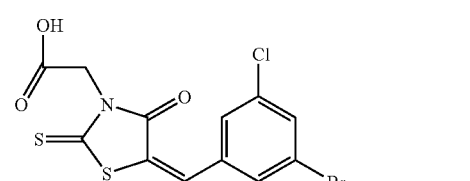 2 | 3.4 | >100 | >100 | >100 | 4 |
| 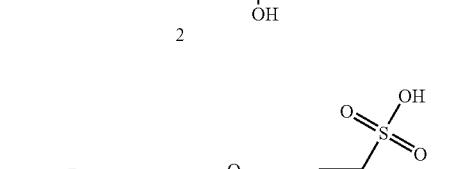 3 | 3.5 | >100 | >100 | >100 | 15 |

TABLE 2-continued

IC$_{50}$ of inhibitors against selected enzymes

| Compounds | IC$_{50}$ (μM) | | | | |
|---|---|---|---|---|---|
| | MurG | OGT | MurA | PBP1b | GftB |
| 4 | 6.4 | >100 | >100 | >100 | 11 |
| 5 | 1.4 | >100 | >100 | >100 | 50 |
| 6 | 4.0 | >100 | >100 | >100 | 100 |
| 7 | 5.4 | >100 | >100 | >100 | 100 |

*No inhibition was observed any concentration, but this compound aggregates at higher concentration.

The compounds were tested in duplicate or in triplicate at three different concentrations, ranging from 5 μM to 100 μM. None of the compounds inhibited OGT, MurA, or PBP1b. Since the first two of these enzymes utilize UDP-GlcNAc substrates, these results show that it is possible to screen for displacement of UDP-GlcNAc from one enzyme without selecting for compounds that bind to all UDP-GlcNAc processing enzymes. Inhibitors that are relatively rigid, as most of the hit compounds we have identified are, would not be expected to bind equivalently to enzymes with differently shaped active sites even if they displace the same substrate. For example, compound 1, which is a competitive inhibitor of MurG with respect to UDP-GlcNAc, is selective for MurG by a factor of at least 30. Although MurG and GtfB have very similar folds, their amino acid compositions are quite different and there are many differences in the details of the donor binding sites. Based on the experimental results as well as structural considerations, the identification of inhibitors from the glycosyl donor displacement screen is now fundamental.

Compounds

The compounds herein described may have asymmetric centers. Compounds of the present invention that contain an asymmetrically substituted atom may be isolated in optically active or racemic forms. It is well know in the art how to prepare optically active forms, such as by resolution of racemic forms or by synthesis from optically active starting materials. Many geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms. All chiral, diastereomeric, racemic forms and all geometric isomeric forms of a structure are intended, unless the specific stereochemistry or isomeric form is specifically indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced.

When any variable (e.g., $R^a$) occurs more than one time in any constituent or formula for a compound, its definition at each occurrence is independent of its definition at every other occurrence. Thus, for example, if a group is shown to be substituted with 0-2 $R^a$, then said group may optionally be substituted with up to two $R^a$ groups and $R^a$ at each occurrence is selected independently from the definition of $R^a$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "$C_{1-8}$ alkyl" is intended to include both branched and straight-chain saturated aliphatic hydrocarbon groups having the specified number of carbon atoms, examples of which include, but are not limited to, methyl, ethyl, n-propyl, i-propyl, n-butyl, i-butyl, sec-butyl, t-butyl, pentyl, and hexyl. $C_{1-8}$ alkyl, is intended to include $C_1$, $C_2$, $C_3$, $C_4$, $C_5$, $C_6$, $C_7$, and $C_8$ alkyl groups. "Alkenyl" is intended to include hydrocarbon chains of either a straight or branched configuration and one or more unsaturated carbon-carbon bonds which may occur in any stable point along the chain, such as ethenyl, propenyl, and the like. "Alkynyl" is intended to include hydrocarbon chains of either a straight or branched configuration and one or more unsaturated triple carbon-carbon bonds which may occur in any stable point along the chain, such as ethynyl, propynyl, and the like. "$C_{3-6}$ cycloalkyl" is intended to include saturated ring groups having the specified number of carbon atoms in the ring, including mono-, bi-, or poly-cyclic ring systems, such as cyclopropyl, cyclobutyl, cyclopentyl, cyclohexyl, and cycloheptyl in the case of $C_7$ cycloalkyl. $C_{3-6}$ cycloalkyl, is intended to include $C_3$, $C_4$, $C_5$, and $C_6$ cycloalkyl groups.

"Halo" or "halogen" as used herein refers to fluoro, chloro, bromo, and iodo' and "haloalkyl" is intended to include both branched and straight-chain saturated aliphatic hydrocarbon groups, for example $CF_3$, having the specified number of carbon atoms, substituted with 1 or more halogen (for example —$C_vF_w$ where v=1 to 3 and w=1 to (2v+1)).

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl,; [3.3.0]bicyclooctane, [4.3.0]bicyclononane, [4.4.0]bicyclodecane(decalin), [2.2.2]bicyclooctane, fluorenyl, phenyl, naphthyl, indanyl, adamantyl, or tetrahydronaphthyl(tetralin).

As used herein, the term "heterocycle" or "heterocyclic system" is intended to mean a stable 5, 6, or 7-membered monocyclic or bicyclic or 7, 8, 9, or 10-membered bicyclic heterocyclic ring which is saturated, partially unsaturated or unsaturated (aromatic), and which consists of carbon atoms and 1, 2, 3, or 4 heteroatoms independently selected from the group consisting of N, NH, O and S and including any bicyclic group in which any of the above-defined heterocyclic rings is fused to a benzene ring. The nitrogen and sulfur heteroatoms may optionally be oxidized. The heterocyclic ring may be attached to its pendant group at any heteroatom or carbon atom which results in a stable structure. The heterocyclic rings described herein may be substituted on carbon or on a nitrogen atom if the resulting compound is stable. If specifically noted, a nitrogen in the heterocycle may optionally be quaternized. It is preferred that when the total number of S and O atoms in the heterocycle exceeds 1, then these heteroatoms are not adjacent to one another. As used herein, the term "aromatic heterocyclic system" is intended to mean a stable 5 to 7-membered monocyclic or bicyclic or 7 to 10-membered bicyclic heterocyclic aromatic ring which consists of carbon atoms and from 1 to 4 heteroatoms independently selected from the group consisting of N, O and S.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like.

Preferred compounds that antagonize the activity of nucleotide-sugar glycosyltransferases identified by methods of the present invention have a 5-membered, nitrogen-containing heterocyclic core with an alkyl or aryl substituent at N-1 and an arylidene substituent at the 3 position.

Compositions are preferred which comprise an effective amount of a compound of Formula I, or a stereoisomer, or pharmaceutically acceptable salt thereof, that inhibits the ability of a glycosyltransferase to bind a substrate, in a pharmaceutically acceptable carrier,

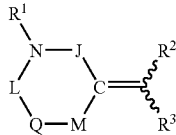
(I)

wherein:
J is selected from C=O, S, NH, C=S, $CH_2$, CH $R^1$, and C $R^1R^1$;
M is selected from C=O, S, C=S, CH $R^1$, and $CR^1R^1$;
L is selected from C=O, NH, C=S, S, CH $R^1$, $CR^1R^1CHR^2$, $CR^2R^2$, =N—, —C(=$NR^1$)—, and —C($R^1$)=;
Q is absent or selected from —NH—, and —$NR^1$;
$R^1$, is selected from H, $C_{1-6}$ alkyl, $C_{2-8}$ alkenyl, $C_{2-8}$ alkynyl, F, Cl, Br, I, $NO_2$, CN, $(CH_2)_rOH$, $(CH_2)_rSH$, $(CH_2)_rOR^{1d}$, $(CH_2)_rSR^{1d}$, $(CH_2)_rNR^{1a}R^{1a'}$, $(CH_2)_rC(O)OH$, $(CH_2)_rC(O)R^{1b}$, $(CH_2)_rC(O)NR^{1a}R^{1a}$, $(CH_2)_rNR^{1a}C(O)R^{1a}$, $(CH_2)_rNR^{1a}C(O)H$, $(CH_2)_rNR^{1a}C(O)NHR^{1a}$, $(CH_2)_rC(O)OR^{1b}$, $(CH_2)_rOC(O)R^{1b}$, $(CH_2)_rOC(O)NHR^{1a}$, $(CH_2)_rS(O)_2OH$, $(CH_2)_rS(O)_2NR^{1a}R^{1a'}$, $(CH_2)_rNR^{1a}S(O)_2R^{1b}$, $C_{1-6}$ haloalkyl, a $(CH_2)_r$—$C_{3-13}$ carbocyclic residue substituted with 0-5 $R^{1c}$, and a $(CH_2)_r$-5-10 membered heterocyclic system containing 1-4 heteroatoms selected from N, O, and S, substituted with 0-3 $R^{1c}$;
$R^{1a}$ and $R^{1a'}$, at each occurrence, are selected from H, $C_{1-6}$ alkyl, $C_{2-8}$ alkenyl, $C_{2-8}$ alkynyl, a $(CH_2)_r$—$C_{3-10}$ carbocyclic residue substituted with 0-5 $R^{1e}$, and a $(CH_2)_r$-5-10 membered heterocyclic system containing 1-4 heteroatoms selected from N, O, and S, substituted with 0-3 $R^{1e}$;
$R^{1b}$, at each occurrence, is selected from $C_{1-6}$ alkyl, $C_{2-8}$ alkenyl, $C_{2-8}$ alkynyl, a $(CH_2)_r$—$C_{3-6}$ carbocyclic residue substituted with 0-2 $R^{1e}$, and a $(CH_2)_r$-5-6 membered heterocyclic system containing 1-4 heteroatoms selected from N, O, and S, substituted with 0-3 $R^{1e}$;
$R^{1c}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rNR^{1f}R^{1f}$, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{1b}$, $(CH_2)_rC(O)NR^{1f}R^{1f}$, $(CH_2)_rNR^{1f}C(O)R^{1a}$, $(CH_2)_rC(O)OC_{1-4}$ alkyl, $(CH_2)_rOC(O)R^{1b}$, $(CH_2)_rC(=NR^{1f})NR^{1f}R^{1f}$, $(CH_2)_rS(O)_pR^{1b}$, $(CH_2)_rNHC(=NR^{1f})NR^{1f}R^{1f}$, $(CH_2)_rS(O)_2NR^{1f}R^{1f}$, $(CH_2)_rNR^{1f}S(O)_2R^{1b}$, and $(CH_2)_r$phenyl substituted with 0-3 $R^{1e}$;
$R^{1d}$, at each occurrence, is selected from $C_{1-6}$ alkyl, $C_{2-6}$ alkenyl, $C_{2-6}$ alkynyl, a $C_{3-10}$ carbocyclic residue substituted with 0-3 $R^{1c}$, and a 5-6 membered heterocyclic system containing 1-4 heteroatoms selected from the group consisting of N, O, and S substituted with 0-3 $R^{1c}$;
$R^{1e}$, at each occurrence, is selected from $C_{1-6}$ alkyl, $C_{2-8}$ alkenyl, $C_{2-8}$ alkynyl, $(CH_2)_rC_{3-6}$ cycloalkyl, Cl, F, Br, I, CN, $NO_2$, $(CF_2)_rCF_3$, $(CH_2)_rOC_{1-5}$ alkyl, OH, SH, $(CH_2)_rSC_{1-5}$ alkyl, $(CH_2)_rNR^{1f}R^{1f}$, and $(CH_2)_r$phenyl;
$R^{1f}$, at each occurrence, is selected from H, $C_{1-6}$ alkyl, and $C_{3-6}$ cycloalkyl;
R2 is selected from $(CH_2)_r$—$C_{5-10}$ carbocyclic residue substituted with 0-7 $R^{2a}$, and a $(CH_2)_r$-5-10 membered heterocyclic system optionally containing C=O and 1-4 heteroatoms selected from N, O, and S, wherein the heterocyclic system is substituted with 0-7 $R^{2a}$;
$R^{2a}$, at each occurrence, is selected from H, $C_{1-6}$ alkyl, $C_{2-8}$ alkenyl, $C_{2-8}$ alkynyl, $(CH_2)_rC_{3-6}$ cycloalkyl, Cl, Br, I, F, $(CF_2)_rCF_3$, $NO_2$, CN, $(CH_2)_rOH$, $(CH_2)_rOC_{1-4}$ alkyl, $(CH_2)_rSC_{1-4}$ alkyl, $(CH_2)_rC(O)OH$, $(CH_2)_rC(O)R^{9b}$, $(CH_2)_rC(O)NR^{1f}R^{1f}$ and $(CH_2)_r$ phenyl wherein the phenyl on the $(CH_2)_r$ phenyl is substituted with 0-5 substituents selected from F, Cl, Br, I, $NO_2$, $C_{1-6}$ alkyl, OH, $(CH_2)_rC(O)OH$, $(CH_2)_rC(O)OC_{1-4}$ alkyl, $NR^{2b}R^{2b}$, and $(CH_2)_rS(O)_2NR^{2b}R^{2b}$.
$R^{2b}$, at each occurrence, is selected from H, $C_{1-6}$ alkyl, and $C_{3-6}$ cycloalkyl; and
R3 is selected from H;
alternatively $R^2$ and $R^3$ join to form a 5-10 membered heterocyclic system optionally containing C=O and 1-4 heteroatoms selected from N, O, and S, wherein the heterocyclic system is substituted with 0-7 $R^{2a}$.

An example composition of the present invention comprises compound 1:

Compound 1

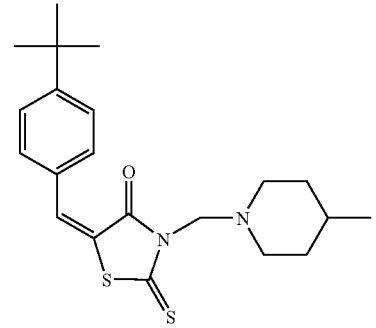

(5-(4-tert-Butyl-benzylidene)-3-(4-methyl-piperidin-1-ylmethyl)-2-thioxo-thiazolidin-4-one)

This compound is a competitive inhibitor of MurG with respect to the UDP-GlcNAc substrate. Other example compositions of the present invention comprise, for example, an effective amount of a compound selected from the group consisting essentially of [5-(3-Bromo-5-chloro-2-hydroxy-benzylidene)-4-oxo-2-thioxo-thiazolidin-3-yl]-acetic acid;
2-[5-(1-Benzyl-5-bromo-2-oxo-1,2-dihydro-indol-3-ylidene)-4-oxo-2-thioxo-thiazolidin-3-yl]-ethanesulfonic acid;
5-(5-Bromo-furan-2-ylmethylene)-1-(4-chloro-phenyl)-pyrimidine-2,4,6-tirone;
5-{3-[1-(3-Chloro-phenyl)-4,6-dioxo-2-thioxo-tetrahydro-pyrimidin-5-ylidenemethyl]-2,5-dimethyl-pyrrol-1-yl}-isophthalic acid;
5-{3-[2-(4-tert-Butyl-phenoxy)-ethoxy]-benzylidene}-2-thioxo-dihydro-pyrimidine-4,6-dione;
4-{3-[5-(4-Bromo-phenyl)-furan-2-ylmethylene]-2-oxo-5-phenyl-2,3-dihydro-pyrrol-1-yl}-benzoic acid;
3-Azepan-1-ylmethyl-5-(4-methyl-benzylidene)-2-thioxo-thiazolidin-4-one;

2-[5-(4-Chloro-benzylidene)-2,4-dioxo-thiazolidin-3-yl]-N-(2-hydroxy-5-nitro-phenyl)-acetamide;

2-[5-(5-Bromo-2-oxo-1,2-dihydro-indol-3-ylidene)-4-oxo-2-thioxo-thiazolidin-3-yl]-3,4-dimethyl-pentanoic acid;

N-[5-(5-Nitor-2-oxo-1,2-dihydro-indol-3-ylidene)-4-oxo-2-thioxo-thiazolidin-3-yl]-nicotinamide;

3-[3-(1-Carboxy-2-phenyl-ethyl)-4-oxo-2-thioxo-thiazolidin-5-ylidene-]2-oxo-2,3-dibydro-indole-1-carboxylic acid;

3-[3-(4-Oxo-5-thiophen-2-ylmethylene-2-thioxo-thiazolidin-3-yl)-propionylamino]-benzoic acid;

2-[5-(1-Benzyl-5-bromo-2-oxo-1,2-dihydro-indol-3-ylidene)-4-oxo-2-thioxo-thiazolidin-3-yl]-ethanesulfonic acid;

[5-(3-Bromo-5-chloro-2-hydroxy-benzylidene)-4-oxo-2-thioxo-thiazolidin-3-yl]-acetic acid;

5-(5-Bromo-3-chloro-2-hydroxy-benzylidene)-2-phenylimino-thiazolidin-4-one;

2-(3,5-Dimethyl-phenylimino)-5-(4-hydroxy-3-methoxy-5-nitro-benzylidene)-thiazolidin-4-one;

{3-[2-(2-Chloro-phenylimino)-4-oxo-thiazolidin-5-ylidenemethyl]-phenoxy}-acetic acid;

2-(2-Chloro-phenylimino)-5-(2-hydroxy-3-nitro-benzylidene)-thiazolidin-4-one;

2-(2-Chloro-phenylimino)-5-(4-nitro-benzylidene)-thiazolidin-4-one;

4-[(2-Methoxy-3,5-dinitro-phenylamino)-methylene]-5-methyl-2-o-tolyl-2,4-dihydro-pyrazol-3-one;

3-{5-Oxo-4-[5-(4-sulfamoyl-phenyl)-furan-2-ylmethylene]-3-trifluronnethyl-4,5-dihydro-pyrazol-1-yl}-benzenesulfonic acid;

2-Chloro-5-[4-(4-hydroxy-3-methoxy-5-nitro-benzylidene)-3-methey-5-oxo-4,5-dihydro-pyrazol-1-yl]-benzoic acid;

5-{4-[5-(2-Carboxy-phenyl)-furan-2-ylmethylene]-3-methyl-5-oxo-4,5-dihydro-pyrazol-1-yl}-2-chloro-benzoic acid;

5-{3-[1-(4-Chloro-phenyl)-4,6-dioxo-2-thioxo-tetrahydro-pyrimidin-5-ylidenemethyl]-2,5-dimethyl-pyrrol-1-yl}-isophthalic acid;

5-(4-Hydroxy-3-methoxy-5-nitro-benzylidene)-2-thioxo-1-p-tolyl-dihydro-pyrimidine-4,6-dione;

1-(3,5-Dimethyl-phenyl)-5(4-hydroxy-3-methoxy-5-nitro-benzylidene)-pyrimidine-2,4,6-trione;

1-(4-Chloro-phenyl)-5-(4-hydroxy-3-methoxy-5-nitro-benzylidene)-2-thioxo-dihydro-pyrimidine-4,6-dione;

1-(4-Bromo-phenyl)-5-(4-hydroxy-3-nitro-benzylidene)-pyrimidine-2,4,6-trione;

5-(3-Chloro-4-hydroxy-5-methoxy-benzylidene)-1-(4-chloro-phenyl)-pyrimidine-2,4,6-trione;

5-(4-Diethylamino-2-methoxy-benzylidene)-2-thioxo-1-o-tolyl-dihydro-pyrimidine-4,6-dione;

5-{3-[1-(2-Fluoro-phenyl)-4,6-dioxo-2-thioxo-tetrahydro-pyrimidin-5-ylidenemethyl]-2,5-dimethyl-pyrrol-1-yl}-isophthalic acid; and 1-(5-Ethoxy-2-methoxy-phenyl)-5-(3-furan-2-yl-allylidene)-pyrimidine-2,4,6-trione;

or a derivative of one of these compounds, or a stereoisomer, or pharmaceutically acceptable salt of one of these compounds; any of which that inhibits the ability of a glycosyltransferase to bind a substrate.

GTases in the endoplasmic reticulum and in the Golgi apparatus are known to be involved in the assembly of the oligosaccharides that are presented on glycoproteins and glycolipids. These glycoproteins and glycolipids mediate a variety of cell-cell recognition events, and it is known from mutational studies and knockout experiments that alterations in the patterns of glycosylation can be pathogenic. However, it has been difficult to probe the roles of individual glycosyltransferases or their products because, with few exceptions, selective glycosyltransferase inhibitors do not exist. Because such compounds would be useful for a variety of purposes, there is great interest in strategies to make GTase inhibitors.

A method for controlling the growth of bacteria is provided, for example, comprising applying an effective amount of a compound of Formula I and/or identified by a method described herein in a carrier composition to a site where control of bacterial growth is needed. The term "site", as used herein, includes but is not limited to mammalian tissue topical application on, e.g., dermatological, optical, nasal, pulmonary, and/or an otherwise exposed site of a wound, lesion, or infection (including eyes, ears, nose, and throat). Pharmaceutically acceptable carriers for these type applications are well-known in the art.

Therapeutic compositions of this invention may include one or more of the Formula I compounds from about 0.01 to 20.0 weight percent, preferably about 1.0 to 5.0 wt %, in an acceptable vehicle. A variety of carriers normally used for topical administration include, for example, surfactants, emulsifiers, stabilizers, emollients, thickeners, neutralizers, lubricants, and/or propellants; and can further comprise preservatives, skin penetration enhancers, humectants, chelating agents, colors and/or fragrances. The composition may be in the form of solutions, water-in-oil or oil-in-water emulsions, suspensions, lotions, creams, sticks, ointments, liposomal complexes, polymer encapsulated powders, surface absorption complexes, aerosols, monomeric and polymeric gels, plasters, patches, films, tapes and other preparation known to those skilled in the art. The amount of carrier may vary from about 80.0 to about 99.99 wt %, preferably from about 95.0 to 99.0% by weight of total composition. To help with the dispersion of active compounds of the present invention, the carrier may contain emulsifiers. The emulsifying portion of the vehicle can be cationic, anionic, nonionic or amphoteric or a combination thereof. Nonionic emulsifiers are preferred. Exemplary nonionic emulsifiers are commercially available sorbitans, alkoxylated fatty alcohols and alkyl polyglycosides. Anionic emulsifiers may include soaps, alkyl sulfates, monoalkyl and dialkyl phosphates, alkyl sulphonates and acyl isethionates. Possible preservatives include parabens, sorbates, benzyl alcohol, diazolidinyl urea and isothiazolinones. Exemplary emollients suitable for the composition include silicon oils, mineral oil, cocoa butter, fatty acid esters, beeswax and lanolin. Examples of suitable thickening agents include xantham gum, xanthamgum-brine tolerant, hydroxypropyl cellulose, hydroxyethyl cellulose, carbopol and gum acacia. An exemplary thickening agent is Sepigel 305 from Seppic Co., France. The composition may also include humectants, for example, glycerin, propylene glycol, polyethylene glycols and urea.

A method is further provided for treating, i.e., controlling, a bacterial infection comprising administering an effective amount of a compound of Formula I and/or identified by a method described herein to a mammal in need of treatment. Compounds of Formula I may be administered orally, intravenously, or topically. A further aspect of the invention provides a pharmaceutical composition comprising a compound of Formula I, or a pharmaceutically acceptable salt or ester thereof and a pharmaceutically acceptable excipient, diluent or carrier. The composition may be in any suitable form, depending on the intended method of administration.

It may for example be in the form of a tablet, capsule or liquid for oral administration, or of a solution or suspension for administration parenterally. The pharmaceutical compositions optionally also include one or more other agents for the treatment of infections. A still further aspect of the invention provides a method of inhibiting a nucleotide-sugar glycosyltransferase, especially MurG, and/or of treating or preventing a bacterial infection, the method involving administering to a human or animal (preferably mammalian) subject suffering from the condition a therapeutically or prophylactically effective amount of the pharmaceutical composition described above or of a compound of Formula I or salt or ester thereof. "Effective amount", as used herein refers to an amount sufficient to cause a benefit to the subject or at least to cause a change in the subject's condition. The dosage rate at which the compound, salt or ester is administered will depend on the nature of the subject, the nature and severity of the condition, the administration method used, etc. Appropriate values are selectable by routine testing. The compound, salt or ester may be administered alone or in combination with other treatments, either simultaneously or sequentially. For instance, it may be administered in combination with effective amounts of antiviral agents, immunomodulators, anti-infectives, or vaccines known to those of ordinary skill in the art. It may be administered by any suitable route, including orally, intravenously, cutaneously, subcutaneously, etc. It may be administered directly to a suitable site or in a manner in which it targets a particular site, such as a certain type of cell. Suitable targeting methods are already known. A further aspect of the invention provides a method of preparation of a pharmaceutical composition, involving admixing one or more compound of Formula I or salt or ester thereof with one or more pharmaceutically acceptable adjuvants, diluents or carriers and/or with one or more other therapeutically or prophylactically active agents.

EXAMPLE I

Figure 3:
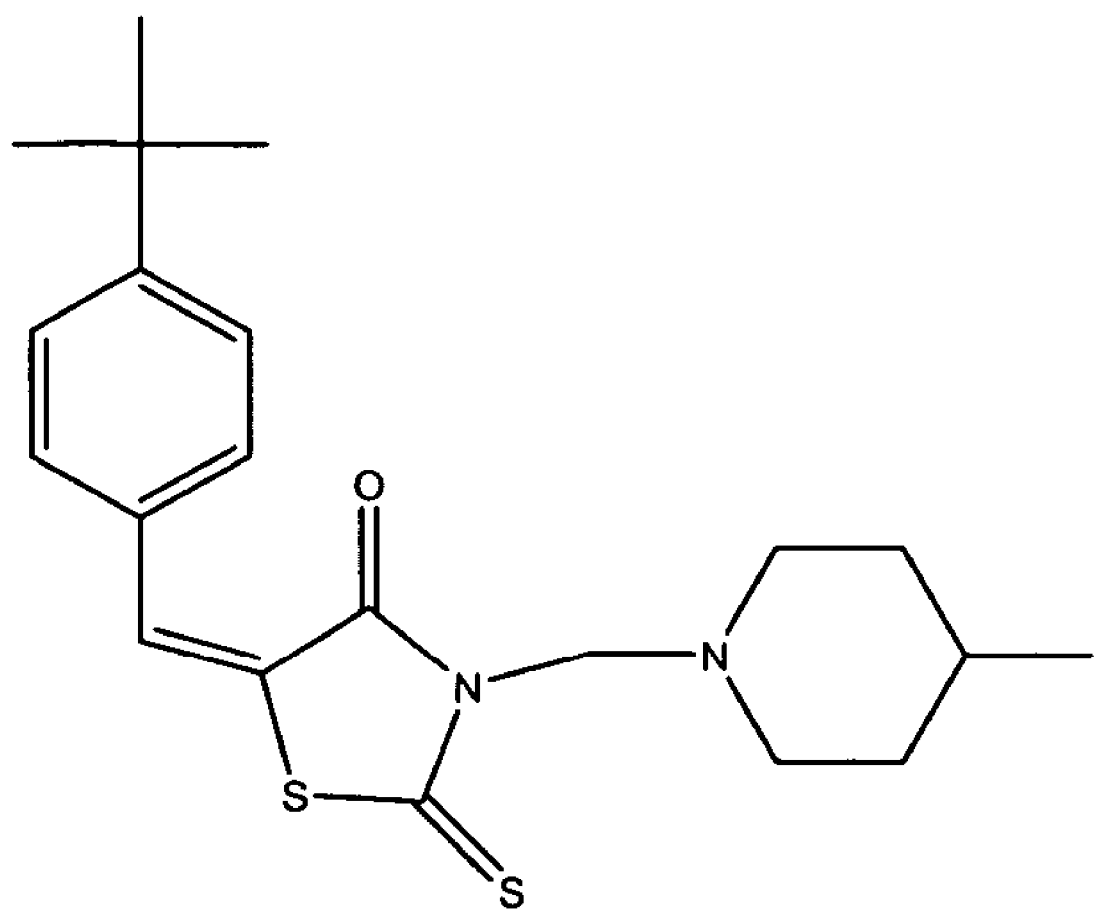
FIG. 3 shows a representative compound, compound 1, of the present invention.
Figure 4:
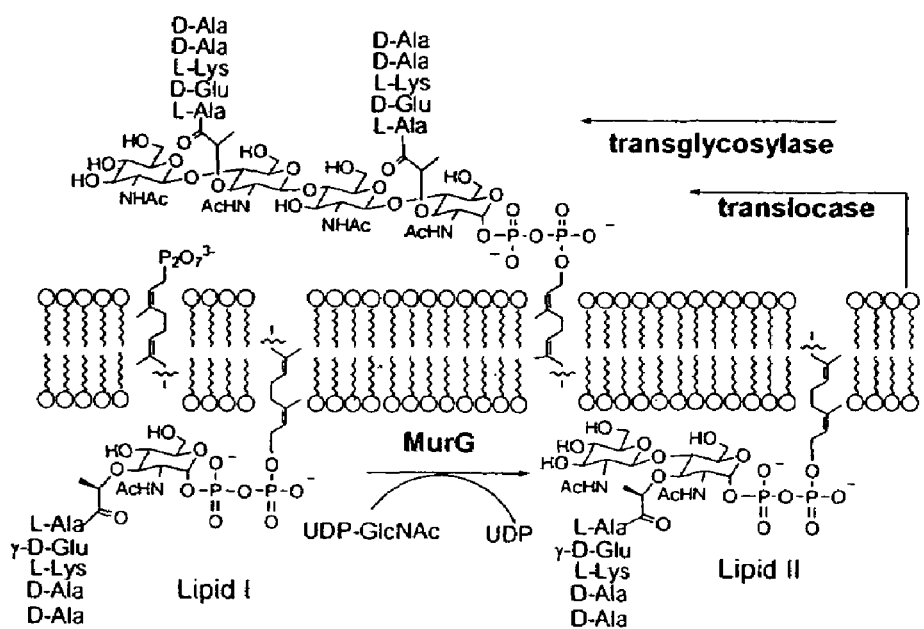
FIG. 4 illustrates how MurG converts Lipid I to Lipid II, which is translocated across the membrane and then polymerized by the transglycosylases.
Figure 5:
FIG. 5 shows a crystal structure of UDP-GlcNAc bound to MurG with the N-acyl group indicated.

A miniaturized fluorescence polarization assay was developed and used to screen 48,877 compounds in duplicate over 5 days. Compounds were screened in 384-well plates. Each plate contained two control wells, one with MurG and F1 (FIG. 2) alone and the other with MurG, F1, and 25 µM UDP. Under the assay conditions, the well containing UDP gave a polarization reading that was approximately 50% that of the wells containing only MurG and F1. Test compounds were added in 100 nL of DMSO to the sample wells to give a final concentration of 25 µg/mL in a final volume of 20 µL. Because the object in this example was to identify ligands that approached or exceeded UDP in binding to MurG, only those wells were scored positive in which the fluorescence signal reproducibly dropped by more than 50%. 44 compounds were selected, representing several different structural classes, for secondary screening using a kinetic assay in which the production of radiolabeled product was measured. Helm, J. S., Chen, L., Walker, S. J. Am. Chem. Soc. 2002, 124, 13970-13971. Compounds were tested in duplicate at a concentration of ~5 µM. At this concentration and under the same assay conditions, UDP inhibited the enzymatic reaction by 50%. The object was to identify compounds that were similar or better inhibitors than UDP, accordingly compounds were selected that reproducibly inhibited the enzyme by more than 50% under the assay conditions. 11 of the 44 compounds met this criterion. 7 of these 11 compounds have a 5-membered, nitrogen-containing heterocyclic core with an alkyl or aryl substituent at N-1 and an arylidene substituent at the 3 position. A representative of the family, and the most potent of the 7 related inhibitors, compound 1, 5-(4-tert-Butyl-benzylidene)-3-(4-methyl-piperidin-1-ylmethyl)-2-thioxo-thiazolidin-4-one, is shown in FIG. 3. Compound 1 is a competitive inhibitor of MurG with respect to the UDP-GlcNAc substrate. The high percentage of inhibitors with a similar core is striking. Manual docking of the inhibitors into the UDP-GlcNAc binding pocket of MurG reveals that the compounds are best accommodated when the 5-membered ring is located in the vicinity of the diphosphate binding site with the N-1 substituent oriented toward the GlcNAc binding site and the arylidene substituent oriented toward the uridine binding site. Thus, by using a NDP-sugar displacement assay, we have identified a family of MurG inhibitors with a neutral core that mimics the diphosphate moiety of UDP-GlcNAc with respect to the display of substituent groups.

EXAMPLE II

High-throughput screens were carried in 384 well plates. The solution containing 50 mM HEPES, pH 8.0, 0.33 µM compound 1 and 2.6 µM MurG was added to the wells. Each plate contained 2 control wells, 1 with MurG and 1 alone and the other with MurG, 1, and 25 µM UDP. Under the assay conditions, the well containing UDP gave a polarization reading that was approximately 50% that of the wells containing only MurG and 1. Test compounds were added in 100 nL of DMSO to the sample wells to give a final concentration of 25 µg/mL in a final volume of 20 µL. About 75,000 compounds were screened in duplicate at the Institute for Chemistry and Cell Biology, a collaborative screening facility located at Harvard Medical School.

EXAMPLE III

Kinetic Assay Used for Secondary Screening.

Assays were carried out by incubating inhibitors at a final concentration of 2.5 µg/mL (~5 µM) at a final concentration of 2.5 µg/mL with 14 µM UDP-$^{14}$C-GlcNAc and 15 µM $C_{20}$ Lipid I analogue (Ye, JACS 123, 3155 (2001)) in 10 µL MurG reaction buffer (50 mM HEPES, pH=7.9, 5 mM $MgCl_2$). Reactions were started by adding 0.5 µL of 0.01 mg/mL MurG stock (in 20 mM Tris, pH=7.9, 150 mM NaCl, and 50 mM EDTA) to the substrate solution, and were quenched after 2 min by adding 10 µL 0.1% SDS and keeping on ice. Products and starting material were separated by cellulose chromatography (3MM Whatman chromatography paper) in isobutyric acid: 1N $NH_4OH$=5:3) and quantitated by scintillation counting.

EXAMPLE IV $IC_{50}$ Measurements.

$IC_{50}$ measurements were carried out using the same assay conditions as above except that inhibitor concentration was varied from 0.5 µM to 20 µM. Data were fit using Prism to the equation:

$$Y = Y_{min} + \frac{Y_{max} - Y_{min}}{1 + 10^{(X - \log C_{50}) * h}},$$

where X is the logarithm of the inhibitor concentration, Y is the reaction rate, and h is the Hill slope.

EXAMPLE V

Inhibition Kinetics.

Compound 2 was subjected to more detailed kinetic analysis using a well known fluorescence-based assay Chen, L., Men, H., Ha, S., Ye, X.-Y., Brunner, L., Hu, Y., Walker, S. Biochemistry 2002; Tetrahedron 58, 6585 (2002). In this assay, the formation of UDP is coupled enzymatically to the oxidation of NADH. Briefly, reactions were carried out in 384-well microplates, and the decrease in NADH fluorescence was monitored at 465 nm using a Perkin-Elmer HTS 700 Plus Bio-Assay Plate Reader. Each reaction contained MurG reaction buffer (50 mM HEPES, pH=7.9, 5 mM $MgCl_2$), 0.5 mM phospho(enol)pyruvate (PEP), 0.2 U/μL lactic dehydrogenase, 3 U/μL pyruvate kinase (added as 10 U/μL stock solution in 100 mM $K_2HPO_4$, pH=7.6), 0.25 mM NADH, 60 μM $C_{20}$ Lipid I analog, an appropriate amount of UDP-GlcNAc, ranging from 40-700 μM (added as an aliquot from a concentrated stock solution in water), and 1 μL enzyme 100-fold diluted from a 10 mg/mL stock (in 20 mM Tris, pH=7.9, 150 mM NaCl, and 50 mM EDTA). Reaction volumes were 30 μL. All the components except for the MurG substrates and MurG were pre-mixed in a reservoir and dispensed into each well. The substrates were then added and the reaction mixtures were incubated for 5 minutes until a stable background rate was achieved. MurG was then added and the fluorescence was monitored for 5-10 min. A time course for each reaction was obtained. The initial rates were determined by calculating the slopes (linear fitting) of the initial linear portion of the reaction time course curves using KaleidaGraph (Synergy Software). Inhibition studies were carried out in duplicate at 2 different concentrations of the inhibitor (2). The $K_i$ was calculated from the replots of the double reciprocal curves using the following equation for competitive inhibition:

$$\frac{1}{v} = \frac{1}{V} + \frac{K_m}{V} \cdot \left(1 + \frac{I}{K_{is}}\right) \cdot \frac{1}{S}.$$

Compound 1 interferes with the NADH fluorescence, and can not be studied using this assay. The inhibition pattern of this compound was determined by using the same kinetic assay used for secondary screening.

EXAMPLE VI

Assay of MurA

MurA was purified following the well-known procedure described by McCoy et al (2003). Cells were grown at 37° C. to $OD_{600}$ (60 mL LB), induced with IPTG for another 6 hrs. Cells were harvested and resuspended in 1.5 mL of 50 mM Tris (pH 7.5)/2 mM dithiothreitol (DTT) and sonicated. Cell debris was removed from the samples by centrifugation at 39,000 rpm for 30 min, and the sample supernatant was desalted using a Pharmacia NAP-10 column equibrated with 50 mM Tris (pH 7.5)/2 mM DTT. The purity of the protein is higher than 90%. The assay mixtures (final volume 50 μL) contained 50 mM Tris (pH7.5), 2 mM DTT, 10 mM UDP-GlcNAc, 20 μg MurA, 2% DMSO and 0, 5, 50, 100 μM inhibitors. The mixtures were preincubated for 15 min at 37° C., and the reaction was started by the addition of 2.5 μL 100 mM PEP. After 30 min of incubation, 800 μL of color reagent was added to stop the reaction. After another 1 min, add 1 μL citrate solution, incubate 30 min at room temperature before measuring $OD_{660}$ by using the reading in absence of UDP-GlcNAc as reference.

EXAMPLE VII

Assays for Transglycosylase PBP1b.

The protein was purified as described. Chen, L., Men, H., Ha, S., Ye, X.-Y., Brunner, L., Hu, Y., Walker, S. Biochemistry 2002; Tetrahedron 58, 6585 (2002). Assays were carried out by separately incubating varying amounts of $^{14}$C-GlcNAc-labeled $C_{35}$ Lipid II (specific activity=273 cpm/pmol) and inhibitors in eppendorf tubes containing 9 μL of buffer (50 mM HEPES at pH 7.5, 10 mM $CaCl_2$, 1000 U/mL penicillin G, 0.2 mM decyl PEG, and 11% DMSO), and 1 μL PBP1b (from a solution freshly prepared by diluting the 50% glycerol stock 20-fold into 5 mM Tris buffer, pH 8.0, containing 8 mM decyl PEG) for 10 min. Reactions were started by adding 1 μL of the above PBP1b mixture to the substrate solution, and were typically stopped after 15 min by adding 10 μL ice cold 10 mM Tris (pH 8.0) containing 0.2% Triton X-100. Reactions were left on ice until spotted on cellulose chromatography paper (3M Whatman chromatography paper). Products and starting material were separated following the works of Anderson et al. using chromatography (isobutyric acid: 1N $NH_4OH$=5:3) and quantitated by scintillation counting. Biochemistry 53, 881 (1965).

EXAMPLE VIII

Assays for GtfB.

GtfB was overexpressed and purified as previously described by Losey in 2001. Inhibitors, dissolved in DMSO, were added at the indicated concentrations to 20 μL reactions containing 50 nM GtfB, 2 mM UDP-glucose, 75 mM Tricine (pH 9), 4 mM TCEP and 600 μM vancomycin aglycone. For consistency, all reactions contained 5% DMSO. Reactions were incubated at 37° C. for 1.5 hr, then quenched with 20 μL cold methanol and centrifuged at 13,000 rpm for 10 min. Reaction mixtures were resolved by analytical HPLC, using a gradient of 0-45% acetonitrile in water/0.1% TFA over 15 min, at a flow rate of 1 mL per minute. Product formation was monitored by UV absorbance at 285 nM.

EXAMPLE IX

Assay for OGT.

The mitochondrial splice variant of OGT, minus the first 50 amino acids, was cloned into pET 32b, and expressed from Novagen BL21 (DE3) cells. The pellet was lysed with B-PER (Pierce) and rLysozyme (Novagen) and the soluble fraction was purified using His-Bind Resin (Novagen). Assay reaction buffer was 10 mM Tris pH 7.4 with 100 μg/mL BSA. A 17 mer peptide substrate was employed at 1 mM concentration. $^{14}$C UDP-GlcNAc (300 mCi/mmole specific activity) was added to a final concentration of 11 μM. Inhibitors tested were added in 0.5 μL of DMSO and the final reaction volume was 20 μL. The reactions were quenched after 50 min at room temperature with 10 μL of formic acid and spotted onto phosphocellulose (Whatman P81) paper disks. The disks were washed for 3×5 min with 1% phosphoric acid, 1 min with acetone and dried before counting. The samples were measured by liquid scintillation counting.

EXAMPLE X

Synthetic Route and Characterization of F1.

Figure 9:
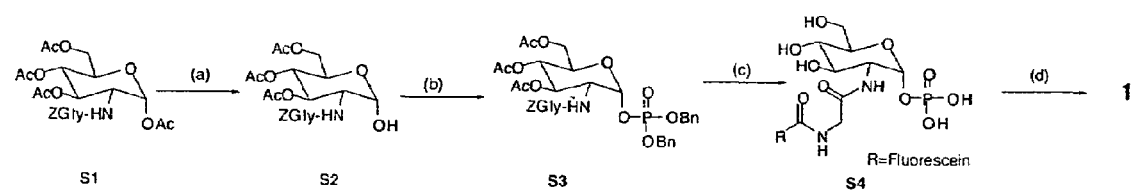
FIG. 9 illustrates an example synthetic route to F1.

See FIG. 9.

$^1$H NMR D$_2$O, 500 MHz of the aromatic and anomeric region:

8.3 (H4 fluorescein, s), 8.12-8.10 (H6 fluorescein, d, J=7.8 Hz), 7.87-7.85 (H6 uracil d, J=8.1 Hz), 7.48-7.46 (H1 d, J=7.8 Hz), 7.31-7.29 (b-fluorescein, 2 protons, dd, J=1.5 Hz, 9.2), 6.88 (c-fluorescein, 2 protons, s), 6.82-6.80 (a-fluorescein, two protons, d, 9.5 Hz), 5.84-5.83 (2×H5' ribose, H5 uracil, m, br), 5.57 (H1, hexose, m, br) ESI-MS (M-1):

979.6, expected 979.67 (a) S1(1.5 g, 2.8 mmole), hydrazine acetate (4.2 mmole), DMF (20 mL), 2 hrs, 60° C., 87% yield. (b) (1) S2 (1.22 g, 2.5 mmole), tetrazole (10 mmole), and dibenzyl N,N disiopropylphosphoramidite (5 mmole), CH$_2$Cl$_2$ (25 mL) –50° C. to –10° C., 1 hr. (2) MCPBA (12.5 mmole), –60° C. to room temperature, 2.5 hrs. Quench, NaSO$_3$, saturated sodium bicarbonate (aq), 84% yield, two steps. (c) (1) S3 (160 mg, 0.211 mmol), 10% Pd/carbon (160 mg), MeOH (5 mL). Stir vigorously under H$_2$, 2.5 hr.

Filter through celite, remove solvent. (2) Redissolve residue (0.11 mmol) in 4.5 mL MeOH, 0.5 mL H$_2$O, add K$_2$CO$_3$ (30 mg, 0.22 mmole), 12 hrs, room temperature, remove solvent under vacuum. (3) Redissolve residue from previous reaction in H$_2$O, adjust pH to 9 using 1M HCl. Add 500 uL 0.1 M NaHCO$_3$, 500 µL dioxane, 30 mg fluorescein-NHS (0.6 mmol, mixed 5,6 isomers). After 30 minutes, add an additional 15 mg (0.3 mmol) fluorescein-NHS. Stir 2 hrs, room temperature. Purify using C18 HPLC (0.1% ammonium bicarbonate in water (A) and methanol (B) mobile phase, t=0, % B=0; t=15, % B=0; t=55, % B=50), 60% yield over three steps. (d) S4 (TEA salt, 10 mg, 0.015 mmol), UMP-mopholidate (19 mg, 0.027 mmol), tetrazole (4 mg, 0.053 mmol), 1 mL pyridine, 500 µL DMF, 48 hrs, room temperature, 40% yield.

All publications mentioned in the above specification are herein incorporated by reference. Various modifications and variations of the described compositions and methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described compositions and modes for carrying out the invention which are obvious to those skilled in the art or related fields are intended to be within the scope of the following claims.

What is claimed is:

1. A method of identifying a compound that inhibits the ability of a glycosyltransferase to bind a substrate comprising:
   combining a glycosyltransferase, a labeled substrate, and a compound, in a reaction vessel, under conditions known to be suitable for the glycosyltransferase to bind the labeled substrate,
   measuring the amount of labeled substrate bound to the glycosyltransferase, and comparing the amount to a standardized amount to identify a relative increase or decrease in substrate bound glycosyltransferase, thereby identifying a compound that modulates the ability of the glycosyltransferase to bind the substrate, wherein the glycosyltransferase is a GT-A or GT-B, NDP-glycosyltransferase, the label is fluorescein and, the labeled substrate is the UDP-GlcNAc (hexose donor) analogue:

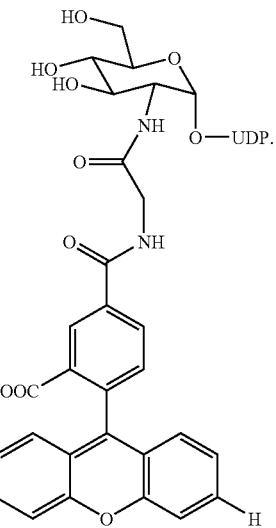

2. A method of identifying a compound that inhibits the ability of a nucleotide-sugar glycosyltransferase to bind a substrate by performing a donor displacement assay comprising: combining in a reaction vessel, under conditions known to be suitable for the glycosyltransferase to bind substrate, a glycosyltransferase, a compound, and a glycosyl donor, wherein at least one substituent on the glycosyl group of said glycosyl donor can be modified to incorporate a label without abolishing binding of the donor to the glycosyltransferase, measuring the amount of labeled glycosyl donor bound to the glycosyltransferase, and comparing the amount to a standardized amount to identify a relative increase or decrease in glycosyl donor bound to the glycosyltransferase, thereby identifying a compound that modulates the ability of the glycosyltransferase to bind the glycosyl donor.

3. The method of claim 2 wherein the donor displacement assay is based on displacement of a fluorescently labeled glycosyl donor.

4. The method of claim 2 wherein the donor displacement assay is based on displacement of a ligand from the glycosyl donor binding site.

5. The method according to claim 2 wherein the glycosyltransferase is a GT-A or GT-B, NDP-glycosyltransferase.

6. The method according to claim 2 wherein the substrate comprises UDP, TDP or GDP.

7. The method according to claim 2 wherein the substrate comprises UDP-GlcNac.

8. The method according to claim 2 wherein the glycosyltransferase is MurG.

9. The method according to claim 2 wherein the label is selected from the group consisting of a chromophore, a fluorophore, a dye, a radioisotope and an enzyme.

10. The method according to claim 9 wherein the label is a fluorophore.

11. The method according to claim 10 wherein the fluorophore is fluorescein.

* * * * *

UNITED STATES PATENT AND TRADEMARK OFFICE
CERTIFICATE OF CORRECTION

| | |
|---|---|
| PATENT NO. | : 7,344,850 B2 |
| APPLICATION NO. | : 10/748335 |
| DATED | : March 18, 2008 |
| INVENTOR(S) | : Kahne et al. |

Page 1 of 1

It is certified that error appears in the above-identified patent and that said Letters Patent is hereby corrected as shown below:

<u>Column 1</u>,
Line 7, before the heading Field Of The Invention, the heading --Statement of Government Funded Research-- should be added. After the heading "Statement of Government Funded Research", --This work was supported by the National Institute of Health Grant Nos. RO/AI 50855, RO/AI 44854 and RO/GM 66174. Accordingly, the Government has certain rights in this invention.-- should be inserted.

Signed and Sealed this

Eighth Day of July, 2008

JON W. DUDAS
*Director of the United States Patent and Trademark Office*